(12) United States Patent
Jang et al.

(10) Patent No.: US 12,014,869 B2
(45) Date of Patent: Jun. 18, 2024

(54) MAGNETIC FIELD DRIVE SYSTEM

(71) Applicant: IUCF-HYU (INDUSTRY-UNIVERSITY COOPERATION FOUNDATION HANYANG UNIVERSITY), Seoul (KR)

(72) Inventors: Gun Hee Jang, Seoul (KR); Won Seo Lee, Yongin-si (KR)

(73) Assignee: IUCF-HYU (INDUSTRY-UNIVERSITY COOPERATION FOUNDATION HANYANG UNIVERSITY), Seoul (KR)

(*) Notice: Subject to any disclaimer, the term of this patent is extended or adjusted under 35 U.S.C. 154(b) by 428 days.

(21) Appl. No.: 17/298,220

(22) PCT Filed: Nov. 1, 2019

(86) PCT No.: PCT/KR2019/014660
§ 371 (c)(1),
(2) Date: May 28, 2021

(87) PCT Pub. No.: WO2020/111539
PCT Pub. Date: Jun. 4, 2020

(65) Prior Publication Data
US 2022/0122752 A1   Apr. 21, 2022

(30) Foreign Application Priority Data

Nov. 28, 2018  (KR) .................. 10-2018-0150004
Mar. 8, 2019   (KR) .................. 10-2019-0026745

(51) Int. Cl.
*H01F 7/20*   (2006.01)
*H01F 7/06*   (2006.01)
(Continued)

(52) U.S. Cl.
CPC ............... *H01F 7/064* (2013.01); *H01F 7/20* (2013.01); *H01F 27/24* (2013.01); *H01F 27/28* (2013.01)

(58) Field of Classification Search
CPC . H01F 7/064; H01F 27/24; H01F 7/06; H01F 7/20; A61B 2017/00345;
(Continued)

(56) References Cited

U.S. PATENT DOCUMENTS

2007/0016006 A1* 1/2007 Shachar ............. A61B 5/062
                                                      600/407
2011/0301497 A1  12/2011 Shachar et al.
(Continued)

FOREIGN PATENT DOCUMENTS

CN    203733601 U    7/2014
JP    2008-503310 A  2/2008
(Continued)

OTHER PUBLICATIONS

Written Opinion for PCT/KR2019/014660 dated Feb. 10, 2020.
International search report for PCT/KR2019/014660 dated Feb. 10, 2020.

*Primary Examiner* — Danny Nguyen
(74) *Attorney, Agent, or Firm* — Sughrue Mion, PLLC

(57) ABSTRACT

A magnetic field drive system is disclosed. The magnetic field drive system comprises: a rail; a first magnetic field generation unit provided on the rail; and a second magnetic field generation unit provided on the rail, and arranged to face the first magnetic field generation unit with a target area therebetween, wherein the first magnetic field generation unit and the second magnetic field generation unit can generate magnetic field in the target area.

16 Claims, 16 Drawing Sheets

(51) Int. Cl.
*H01F 27/24* (2006.01)
*H01F 27/28* (2006.01)

(58) Field of Classification Search
CPC ... A61B 2034/732; A61B 34/35; A61B 17/22;
A61B 2017/00411
USPC .................................. 361/139, 143, 144
See application file for complete search history.

(56) References Cited

U.S. PATENT DOCUMENTS

2013/0303878 A1* 11/2013 Nevo .................. A61B 34/20
600/409
2016/0262841 A1 9/2016 Park et al.

FOREIGN PATENT DOCUMENTS

| KR | 10-1647020 B1 | 8/2016 |
| KR | 10-1740553 B1 | 5/2017 |
| KR | 10-1765015 B1 | 8/2017 |
| WO | 2017-205644 A1 | 11/2017 |

* cited by examiner (A)  (B)

(A)  (B)

MAGNETIC FIELD DRIVE SYSTEM

TECHNICAL FIELD

The present disclosure relates to a magnetic field drive system, and more particularly, to a magnetic field drive system capable of generating a magnetic field in a target area.

BACKGROUND ART

A magnetic robot equipped therein with a magnet is driven when receiving magnetic torque and magnetic force from an external magnetic field generated by a magnetic field drive system, and because the magnetic robot can be remotely controlled precisely, the magnetic robot is applied in various fields, and research and development on the magnetic robot are in progress. For instance, there are a magnetically driven capsule endoscope applied to the digestive system, a magnetic catheter applied to cardiac arrhythmia treatment, and the like. In addition, there are a magnetic robot for vascular treatment for the treatment of obstructive blood vessels, a micro robot for drug delivery in an eyeball, magnetic nanoparticles for targeted drug delivery in tissues, and the like.

As described above, the positions of the human body and lesion portions to which the magnetic robot is applied are very diverse. The key to driving and controlling such a magnetic robot is a magnetic field drive system that generates an external magnetic field. However, in an existing magnetic field drive system, the position and arrangement of the electromagnet that generates the magnetic field are fixed, and thus the position and characteristics of the lesion portion are not considered, so that the magnetic field is inefficiently generated and controlled. In addition, there are limitations that a high-power high-frequency magnetic field cannot be generated due to the magnetic properties of a magnetic structure such as a magnetic core. Such limitations of the magnetic field drive system leads to limitations in diseases that can be dealt with the magnetic robot and motions that can be generated by the magnetic robot.

DISCLOSURE

Technical Problem

The present disclosure provides a magnetic field drive system capable of optimizing the position and arrangement of a magnetic field generation unit according to the location and features of a lesion portion.

In addition, the present disclosure provides a magnetic field drive system capable of generating a high-power high-frequency magnetic field.

Technical Solution

According to the present disclosure, a magnetic field drive system includes a rail; a first magnetic field generation unit installed on the rail; and a second magnetic field generation unit installed on the rail while facing the first magnetic field generation unit with a target area interposed therebetween, wherein the first and second magnetic field generation units may generate a magnetic field in the target area.

In addition, the magnetic field drive system may further include a driving unit configured to move the first and second magnetic field generation units along the rail.

In addition, the first magnetic field generation unit may include a first support frame installed on the rail; at least one first magnetic core supported by the first support frame and having ends disposed toward the target area; and a first coil wound around each of the first magnetic cores, wherein the second magnetic field generation unit includes a second support frame installed on the rail while facing the first support frame; at least one second magnetic core supported by the second support frame and having ends disposed toward the target area; and a second coil wound around each of the second magnetic cores.

In addition, the first magnetic field generation unit may include a first core variable module configured to move the first magnetic core along the first support frame, and the second magnetic field generation unit may include a second core variable module configured to move the second magnetic core along the second support frame.

In addition, the first core variable module may be configured to individually move the first magnetic cores, and the second core variable module may be configured to individually move the second magnetic cores.

In addition, the first core variable module may be configured to linearly move the first magnetic core in a direction of a central axis of the first magnetic core, and the second core variable module may be configured to linearly move the second magnetic core in a direction of a central axis of the second magnetic core.

In addition, the first and second support frames may have ring or arc shapes, respectively, and centers thereof are located on a same axis.

In addition, the first and second magnetic cores, the first and second support frames and the rail may be formed of a magnetic material, and the magnetic field formed in the target area, and magnetic fields formed in the first magnetic core, the first support frame, the rail, the second support frame and the second magnetic core, respectively, may constitute a closed magnetic circuit.

In addition, the magnetic field drive system may further include a power supply unit configured to supply power to the first coil through a first circuit and supply power to the second coil through a second circuit; and variable capacitors provided in the first circuit and the second circuit, respectively.

In addition, the first support frame may have a structure in which a plurality of base frames formed of a magnetic material are stacked.

In addition, the base frames may have a same radius as the first support frame, and are located on a same central axis.

In addition, the first magnetic core may have a structure in which a plurality of base frames formed of a magnetic material are stacked, and the base frames may have a same length as the first magnetic core.

In addition, the rail may have a structure in which a plurality of base frames formed of a magnetic material are stacked, and the base frames may have a same length as the rail.

In addition, the first magnetic core may include a first core housing having an outer side surface around which the first coil is wound, an inner space, and one end in which an opening is formed; a first auxiliary core inserted into the inner space through the opening; and a first core driving unit configured to linearly move the first auxiliary core in a central direction thereof.

In addition, a central axis of the first core housing and a central axis of the first auxiliary core may be located on a same line.

In addition, a central axis of the first core housing may be parallel with a central axis of the first auxiliary core.

In addition, a plurality of openings may be formed at one end of the first core housing, a plurality of first auxiliary cores may be inserted into the openings, respectively, and the first core driving unit may be configured to individually move the first auxiliary cores.

In addition, the openings may have mutually different sizes, and the first auxiliary cores may have sizes corresponding to the openings, respectively.

Advantageous Effects

According to the present disclosure, since the magnetic cores can move along the support frame or linearly move in the axial direction, the generation of the magnetic field can be controlled according to the location and characteristics of the lesion.

Further, according to the present disclosure, it is possible to generate a high-power high-frequency magnetic field in a target region by generating a waste magnetic circuit and providing a variable capacitor and a stacked magnetic structure.

BEST MODE

Figure 1:
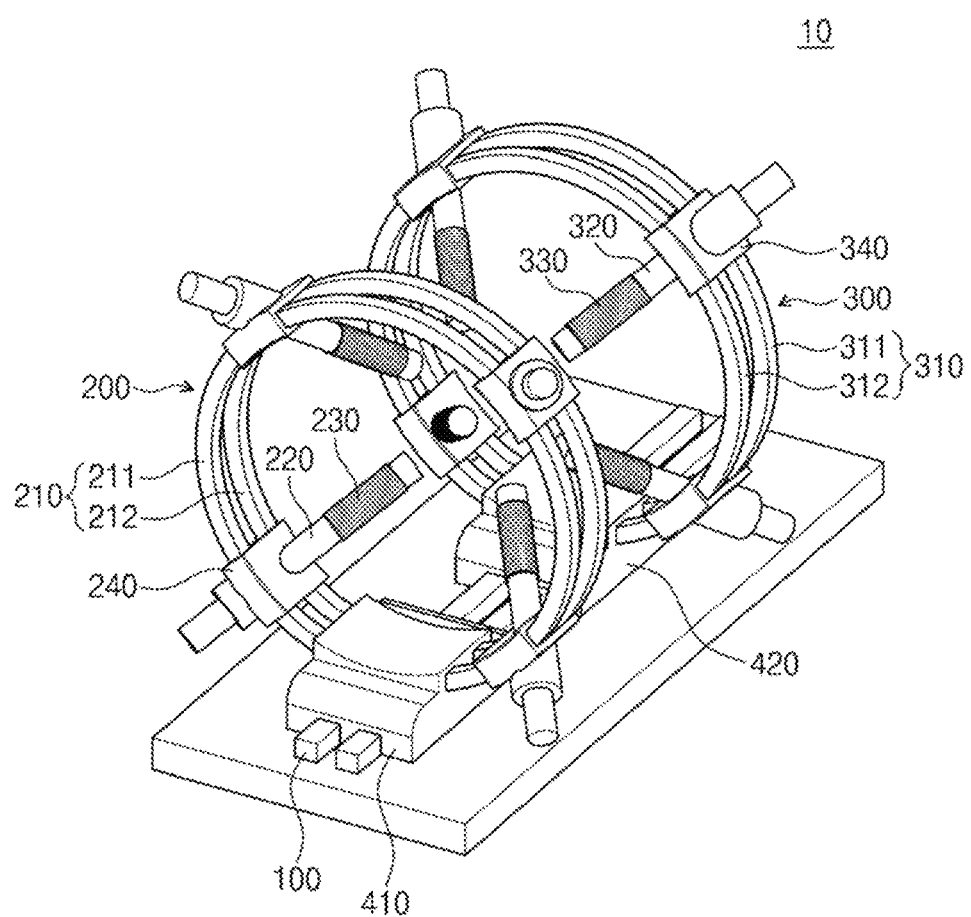
FIG. 1 is a perspective view showing a magnetic field generating system according to an embodiment of the present disclosure.

According to the present disclosure, a magnetic field drive system includes a rail; a first magnetic field generation unit installed on the rail; and a second magnetic field generation unit installed on the rail while facing the first magnetic field generation unit with a target area interposed therebetween, wherein the first and second magnetic field generation units may generate a magnetic field in the target area.

MODE FOR INVENTION

Hereinafter, preferable embodiments of the present disclosure will be described in detail with reference to accompanying drawings. However, the spirit and technical scope of the present disclosure is not limited to the embodiments and may be modified variously in many different forms. Rather, the embodiments introduced herein are provided so that the disclosed contents may be thorough and complete, and the spirit of the present disclosure may be sufficiently conveyed to those skilled in the art.

In the present specification, when it is mentioned that a certain component is on another component, it means that the component may be formed directly on another component or that a third component may be interposed therebetween. In addition, the thicknesses of the lines and the sizes of the components shown in the drawings may be exaggerated for clarity and convenience of explanation.

In addition, in various embodiments of the present specification, terms, such as "first", "second", "third", and the like, are used to describe various components, but these components should not be limited by the terms. These terms are only used to distinguish one component from another component. Accordingly, what is referred to as a first component in one embodiment may be referred to as a second component in another embodiment. Each embodiment described and illustrated herein also includes its complementary embodiment. In the present disclosure, the term "and/or" indicates at least one of components listed before and after.

In the present disclosure, the terms of a singular form may include plural forms unless the context clearly indicates otherwise. In addition, terms such as "include" and/or "have" may be construed to denote a certain characteristic, number, step, operation, constituent element, component or a combination thereof, but may not be construed to exclude the existence of or a possibility of addition of one or more other characteristics, numbers, steps, operations, constituent elements, components or combinations thereof. In the present disclosure, "connection" is used to include both indirectly and direct connection of a plurality of components.

In addition, a detailed description of well-known features or functions will be ruled out in order not to unnecessarily obscure the gist of the present disclosure.

Figure 2:
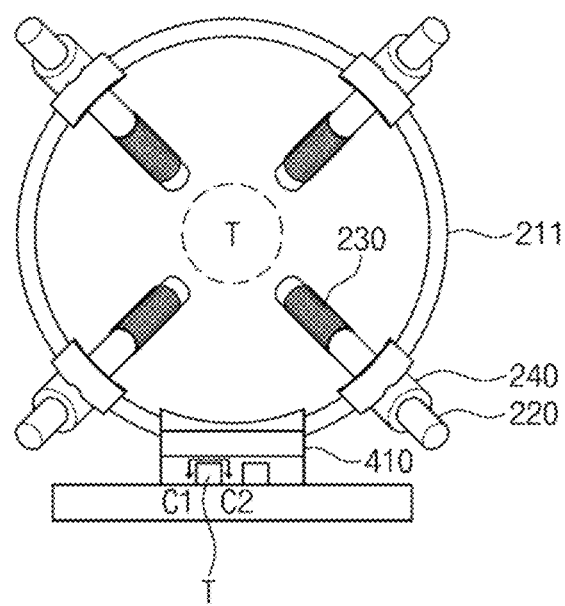
FIG. 2 is a front view of the magnetic field generating system of FIG. 1.

FIG. 1 is a perspective view showing a magnetic field generating system according to an embodiment of the present disclosure. FIG. 2 is a front view of the magnetic field generating system of FIG. 1, FIG. 3 is a right-side view of the magnetic field generating system of FIG. 1.

Figure 3:
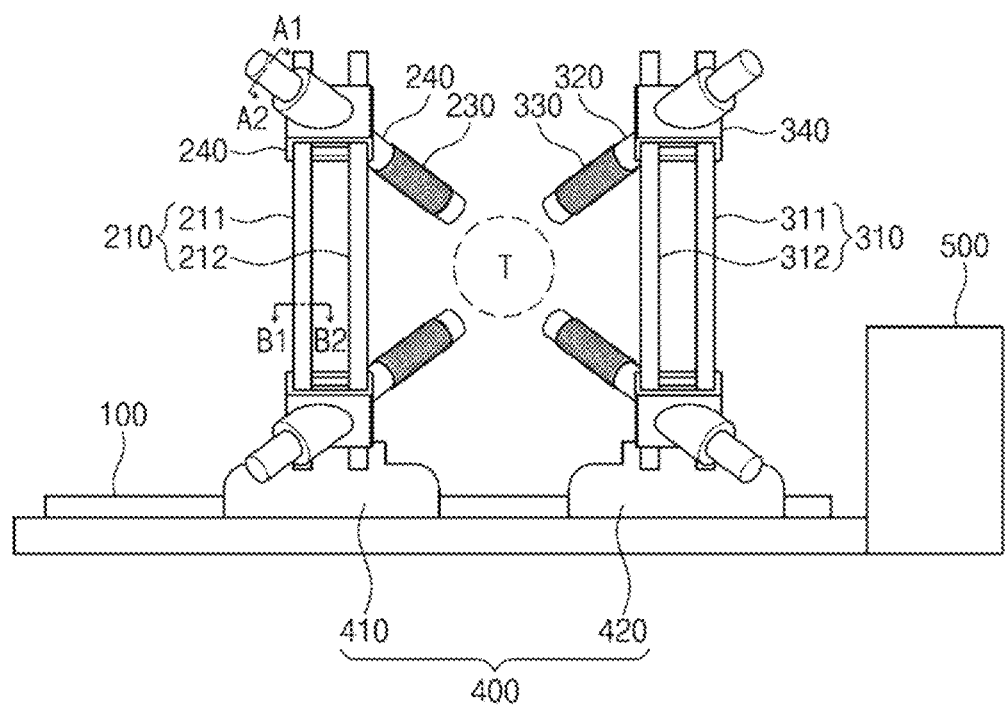
FIG. 3 is a right side view of the magnetic field generating system of FIG. 1.

Referring to FIGS. 1 to 3, the magnetic field generating system generates a magnetic field in a target area. The magnetic field generating system 10 includes a rail 100, a first magnetic field generation unit 200, a second magnetic field generation unit 300, a driving unit 400, and a power supply unit 500.

The rail 100 may have a predetermined length in one direction and be placed on the ground. According to an embodiment, the rail 100 may be formed of a magnetic material.

The first and second magnetic field generation units 200 and 300 are installed on the rail 100, respectively. The first and second magnetic field generation units 200 and 300 are arranged in a line in the length direction of the rail 100. At least an area of the space between the first and second magnetic field generation units 200 and 300 is defined as a target area T. The first and second magnetic field generation units 200 and 300 generate magnetic fields in the target area T.

The first magnetic field generation unit 200 includes a first support frame 210, a first magnetic core 220, a first coil 230, and a first core variable module 240.

The first support frame 210 is installed on the rail 100. The lower end of the first support frame 210 is installed on the rail 100. The first support frame 210 may be formed of a magnetic material. The first support frame 210 is provided as a passage through which the magnetic field generated by the first coil 230 passes. According to an embodiment, the first support frame 210 has a ring shape having a predetermined radius, and its central axis is arranged in parallel with the length direction of the rail 100. According to an example, the first support frame 210 may be provided with a single frame. Alternatively, the first support frame 210 may be provided in a structure in which a pair of frames 211 and 212 are disposed to face each other at a predetermined distance.

The first magnetic core 220 is supported by the first support frame 210 and extends from a predetermined position of the first support frame 210 toward the target area T. The first magnetic core 220 is a magnetic material having a predetermined shape, and the end is disposed toward the target area T. The first magnetic core 220 may have a cylindrical or polygonal column shape. At least one first magnetic core 220 may be provided. According to the embodiment, four first magnetic cores 220 are provided, and are disposed along the circumference of the first support frame 210 while spaced apart from each other by a predetermined interval. Each of the first magnetic cores 220 is inclined such that the ends are disposed toward the target area T.

The first coil 230 is wound around each of the first magnetic cores 220.

The first core variable module 240 is installed on the first support frame 210 and moves the first magnetic core 220. The first core variable module 240 moves the first magnetic core 220 along the circumference of the first support frame 210. In addition, the first core variable module 240 linearly moves the first magnetic core 220 in the direction of the central axis of the first magnetic core 220. The first core variable module 240 is provided to each of the first magnetic cores 220 and individually moves the first magnetic cores 220. As the first magnetic cores 220 move individually along the circumference of the first support frame 210, the interval between the first magnetic cores 220 may be adjusted. The first core variable modules 240 may move the first magnetic cores 220 such that the intervals between the first magnetic cores 220 are the same. Alternatively, the first core variable modules 240 may move the first magnetic cores 220 such that the intervals between the first magnetic cores 220 are different from each other. As the first magnetic cores 220 move forward or backward in the direction of the central axis by driving of the first core variable modules 240, the size of the target area T and the intensity of the magnetic field formed in the target area T may be adjusted. In detail, when the first magnetic cores 220 move forward, the size of the target area T decreases, and a high-intensity magnetic field may be generated in the target area T. To the contrary, when the first magnetic cores 220 move backward, the size of the target area T increases, and a magnetic field having a relatively low intensity may be generated in the target area T. As described above, the size of the target area T and the intensity of the magnetic field formed in the target area T may be adjusted according to the linear movement of the first magnetic cores 220.

The second magnetic field generation unit 300 includes a second support frame 310, a second magnetic core 320, a second coil 330, and a second core variable module 340.

The second support frame 310 is installed on the rail 100. The second support frame 310 has the same shape, material, and size as the first support frame 210, and the lower end is placed on the rail 100. The second support frame 310 faces the first support frame 210, and the central axis is located on the same line as that of the first support frame 210.

The second magnetic core 320 is supported by the second support frame 310 and extends from a predetermined position of the second support frame 310 toward the target area T. The second magnetic core 320 is a magnetic material having the same shape as the first magnetic core 220 and the end is disposed toward the target area T. At least one second magnetic core 320 may be provided. According to an embodiment, the number of second magnetic cores 320 is equal to that of the first magnetic cores 220.

The second coil 330 is wound around the second magnetic cores 320, respectively.

The second core variable module 340 is installed on the second support frame 310 and moves the second magnetic core 320. The second core variable module 340 moves the second magnetic core 320 along the circumference of the second support frame 310. In addition, the second core variable module 340 linearly moves the second magnetic core 320 in the direction of the central axis of the second magnetic core 320. The second core variable module 340 is provided to each of the second magnetic cores 320, and individually moves the second magnetic cores 320.

The driving unit 400 moves the first magnetic field generation unit 200 and the second magnetic field generation unit 300 along the rail 100. The driving unit 400 may individually move the first magnetic field generation unit 200 and the second magnetic field generation unit 300. The driving unit 400 includes a first driving unit 410 for moving the first magnetic field generation unit 200 and a second driving unit 420 for moving the second magnetic field generation unit 300. The first driving part 410 is installed on the rail 100 and is coupled to the first support frame 210. As the first driving unit 410 moves along the rail 100, the first support frame 210 may move. The second driving unit 420 is installed on the rail 100 and is coupled to the second support frame 310. As the second driving unit 420 moves along the rail 100, the second support frame 310 may move. The position and size of the target area T may be adjusted according to the movements of the first and second support frames 210 and 310.

Figure 4:
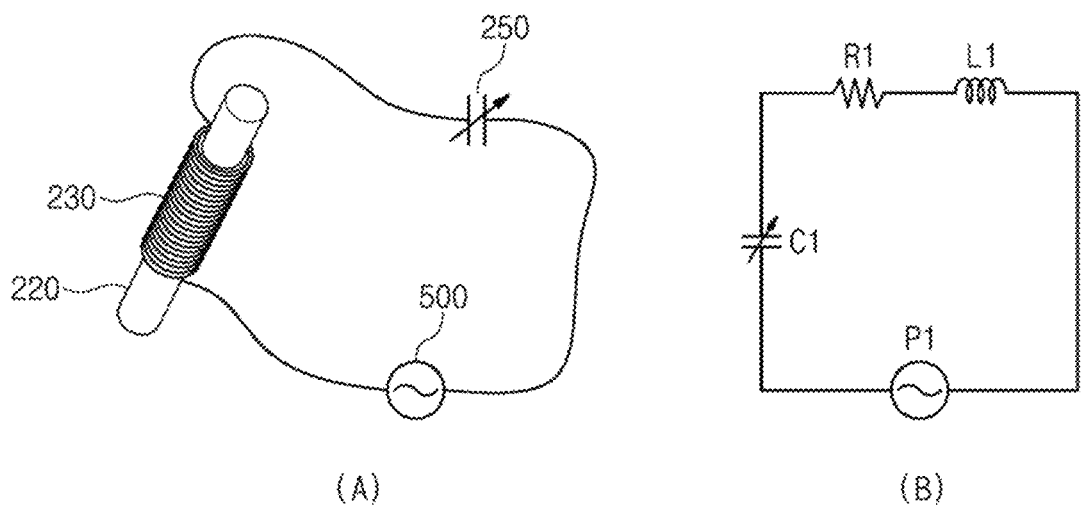
FIG. 4 is a diagram (A) showing a connection (A) between a first magnetic field generation unit and a power supply unit according to an embodiment of the present disclosure, and an electrical circuit diagram (B) thereof.
Figure 5:
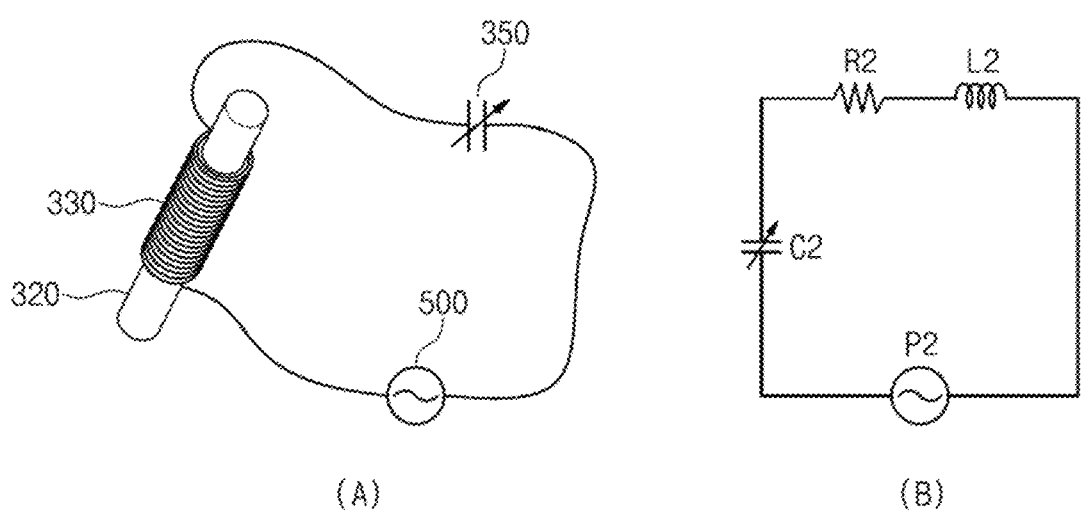
FIG. 5 is a diagram (A) showing a connection between a second magnetic field generation unit and a power supply unit according to an exemplary embodiment of the present disclosure, and an electric circuit diagram (B) thereof.

FIG. 4 is a diagram (A) showing a connection (A) between a first magnetic field generation unit and a power supply unit according to an embodiment of the present disclosure, and an electrical circuit diagram (B) thereof. FIG. 5 is a diagram (A) showing a connection between a second magnetic field generation unit and a power supply unit according to an exemplary embodiment of the present disclosure, and an electric circuit diagram (B) thereof.

Referring to FIGS. 4 and 5, the power supply unit 500 supplies power to the first and second coils 230 and 330. The power supply unit 500 supplies power to a first circuit connected to the first coil 230 and a second circuit connected to the second coil 330, respectively.

The first magnetic field generation unit 200 further includes a first variable capacitor 250 provided to the first circuit 201, and the second magnetic field generation unit 300 further includes a second variable capacitor 350 provided to the second circuit 301. Accordingly, the first and second circuits 201 and 301 are provided in closed circuits including power sources P1 and P2, resistors R1 and R2, inductances L1 and L2, and capacitances C1 and C2. In this case, the power supplies P1 and P2 refer to the power supply unit 500, the 13 resistances R1 and R2 and the inductances L1 and L2 refer to the first and second magnetic cores 220 and 320 and the first and second coils 230 and 330, and the capacitances C1 and C2 refer to the first and second variable capacitors 250 and 350.

The first and second variable capacitors 250 and 350 control the capacitances C1 and C2 of the circuits 201 and 301 to reduce the effects by the inductance L1 and L2 that reduces the intensity of the magnetic field when generating a high-frequency magnetic field. Accordingly, the circuit may generate resonance in which the magnetic field is maximized at a specific frequency. In this case, the resonance point may be adjusted through control of the capacitances C1 and C2 of the first and second variable capacitor 230 and 350. Therefore, it may be possible to generate resonance at any frequency if the range of change of the capacitances C1 and C2 is sufficient.

Therefore, by adjusting the capacitance C1 and/or the capacitance C2 of the first variable capacitor 250 and/or the second variable capacitor 350 to cause resonance occurs at a desired frequency, it is possible to generate a magnetic field at a specific frequency (e.g., the frequency of the input voltage).

In this case, the currents flowing through the first and second coils 230 and 330 may expressed as following Equation 1.

$$I = \frac{V_s}{\sqrt{R_c^2 + \left(2\pi f L_c - \frac{1}{2\pi f C_v}\right)^2}} \quad [\text{Equation 1}]$$

Where $V_s$ denotes the magnitude of an applied voltage, f denotes the frequency of the applied voltage, $R_c$ and $L_c$ denote the resistance and inductance of a coil, and $C_v$ denotes the capacitance of a variable capacitor. The maximum voltage is obtained at the resonant frequency $f_r$ (= $\sqrt{1/4\pi^2 C_v L_c}$) of a closed circuit, and the resonant frequency may be adjusted by the variable capacitor.

Figure 6:
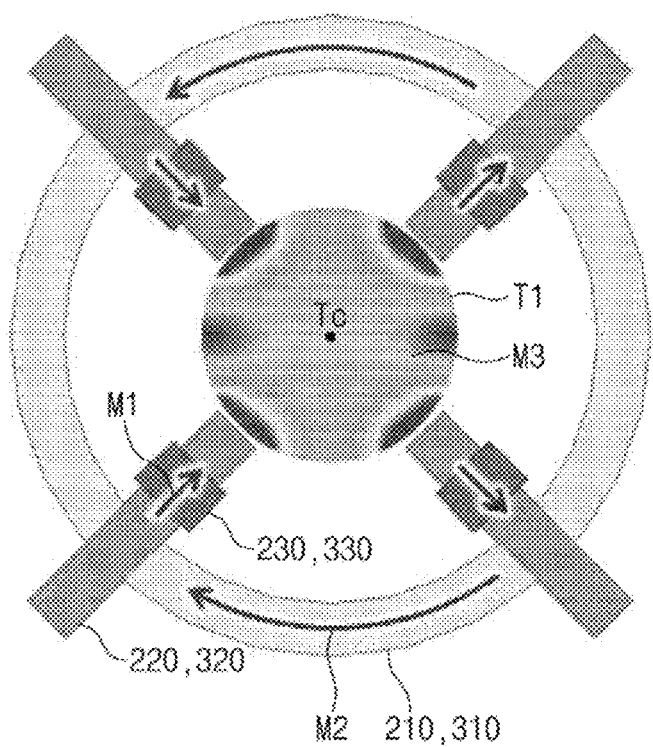
FIGS. 6 and 7 are diagrams showing flows of the magnetic fields generated by first and second magnetic field generation units according to an embodiment of the present disclosure.
Figure 7:
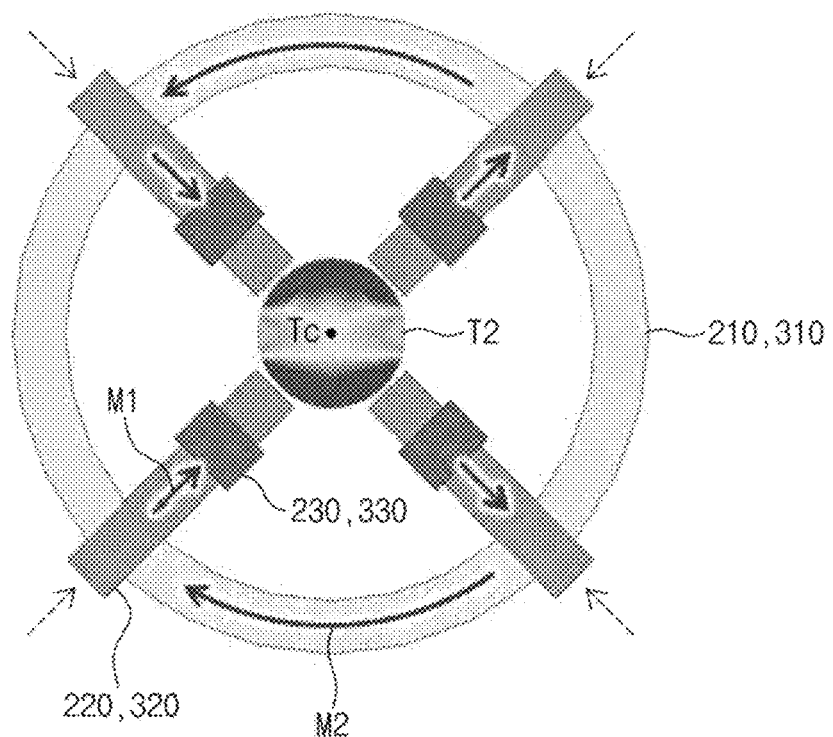
Figure 8:
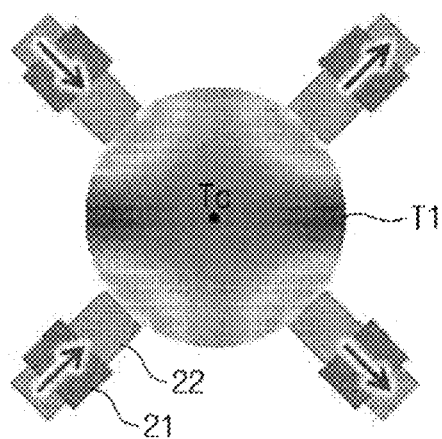
FIG. 8 is a diagram showing a flow of a magnetic field generated by a magnetic field generator according to a comparative example.

FIGS. 6 and 7 are diagrams showing flows of the magnetic fields generated by first and second magnetic field generation units according to an embodiment of the present disclosure. FIG. 8 is a diagram showing a flow of a magnetic field generated by a magnetic field generator according to a comparative example.

First, referring to FIGS. 6 and 7, a magnetic field is generated in the first coil 230 by power supplied from the power supply unit 500, and the generated magnetic field flows through the first magnetic core 220 and the first support frame 210. The magnetic field M1 formed in the first magnetic core 220, the magnetic field M2 formed in the first support frame 210, and the magnetic field M3 formed in the target area T1 form a closed magnetic circuit.

A magnetic field is generated in the second coil 330 by power supplied from the power supply unit 500, and the generated magnetic field flows along the second magnetic core 320 and the second support frame 310. The magnetic field M1 formed in the second magnetic core 320, the magnetic field M2 formed in the second support frame 310, and the magnetic field M3 formed in the target area T2 form a closed magnetic circuit.

FIG. 7 shows that the first and second magnetic cores 220 and 320 are linearly moved in the longitudinal direction by the first and second core variable modules 240 and 340 to form the target area T2 by fitting a lesion portion. As compared with FIG. 6, it is possible to generate a high-intensity magnetic field.

In an actual experimental example, in FIG. 6, the size of the target area T1 is set to a diameter of 500 mm, and in FIG. 7, the size of the target area T2 is set to a diameter of 300 mm, where each coil is wound 1,000 times, and a current of 10 A is approved thereto. The intensity of the magnetic field at the center point Tc of each of the target area T1 and T2 was 27 mT in FIG. 6 and 70 mT in FIG. 7.

Unlike the above, the magnetic field generation unit according to FIG. 8 forms an open magnetic circuit in which the magnetic field generated by the coil 21 is blocked from flowing in the magnetic cores 22. Like in FIG. 6, the size of the target area T1 was set to a diameter of 500 mm, and the winding number of a coil and the applied current were the same as above. As a result, the magnetic field intensity at the center point Tc of the target area T1 was 10 mT.

As described above, it may be understood that the closed magnetic circuit has improved magnetic field generation ability than the open magnetic circuit. In particular, it may be confirmed that a high-intensity magnetic field is effectively generated when a target area is formed by fitting a lesion portion.

Figure 9:
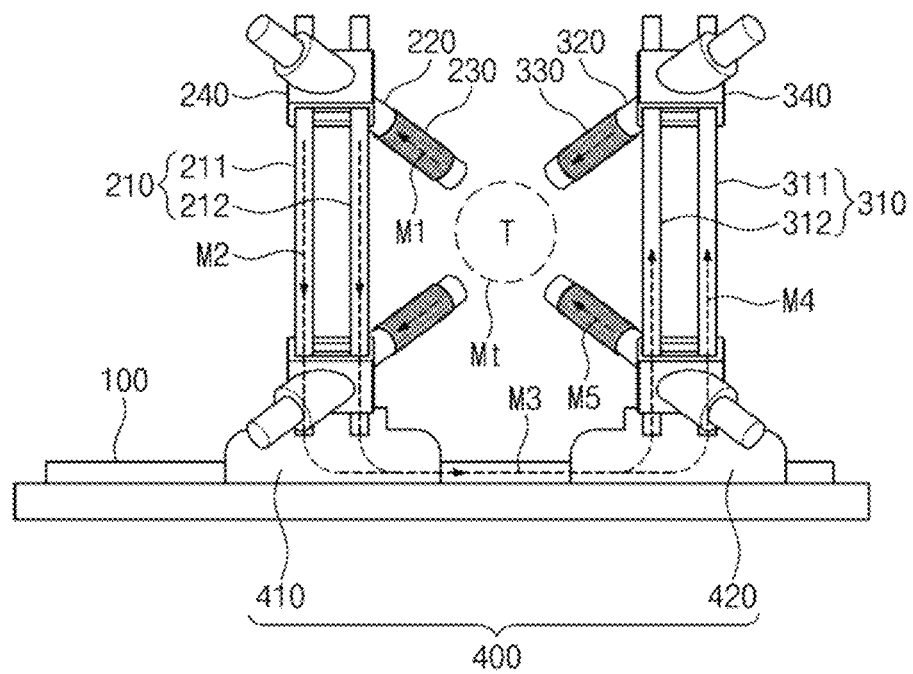
FIG. 9 is a diagram showing a flow of a magnetic field in a magnetic field drive system according to an embodiment of the present disclosure.

FIG. 9 is a diagram showing a flow of a magnetic field in a magnetic field drive system according to an embodiment of the present disclosure.

Referring to FIG. 9, a magnetic field flowing along the first support frame 210 may flow to the second support frame 320 through the rail 100 made of a magnetic material. To the contrary, the magnetic field flowing along the second support frame 320 may flow to the first support frame 210 through the rail. By such a magnetic field flow, the magnetic fields M1 and M2 formed in the first magnetic core 220 and the first support frame 210, the magnetic field M3 formed in the rail 100, the magnetic fields M4 and M5 formed in the second magnetic core 320 and the second support frame 310, and the magnetic field Mt formed in the target area T form a closed magnetic circuit. The formation of the closed magnetic circuit maximizes the magnetic field generation ability in the target area (T).

Figure 10:
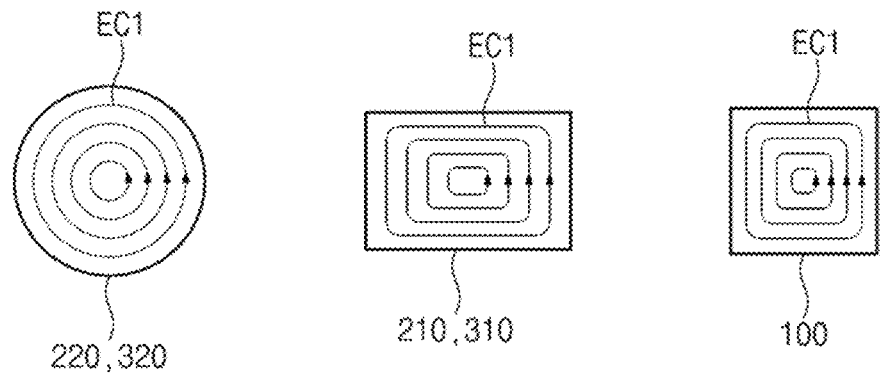
FIG. 10 is a diagram showing each cross section of a magnetic core, a support frame, and a rail according to an embodiment of the present disclosure.
Figure 11:
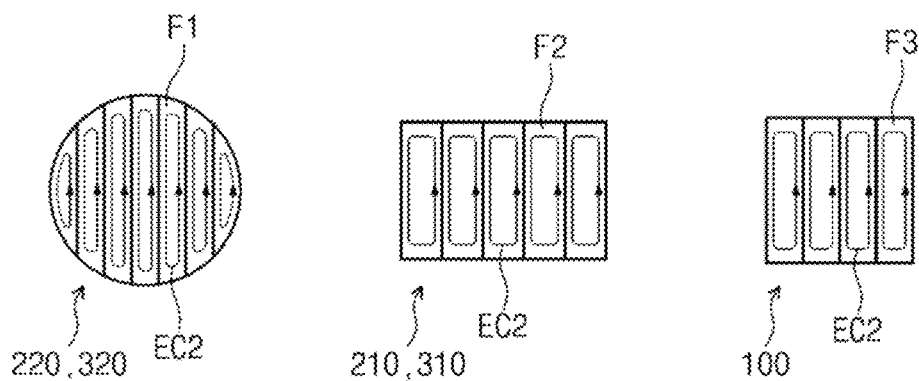
FIG. 11 is a diagram showing each cross section of a magnetic core, a support frame, and a rail according to another embodiment of the present disclosure.

FIG. 10 is a diagram showing each cross section of a magnetic core, a support frame, and a rail according to an embodiment of the present disclosure. FIG. 11 is a diagram showing each cross section of a magnetic core, a support frame, and a rail according to another embodiment of the present disclosure. The cross sections of the magnetic cores 220 and 320 are shown taken along the line A1-A2 of FIG. 3. The cross sections of the support frames 210 and 310 are shown taken along the line B1-B2 of FIG. 3. The cross sections of the rail 100 are shown taken along line C1-C2 of FIG. 2.

First, referring to FIG. 10, the first and second magnetic cores 220 and 320, the first and second support frames 210 and 310, and the rail 100 may be formed with a single frame in a solid form.

Differently, referring to FIG. 11, the first and second magnetic cores 220 and 320 may be formed by stacking a plurality of first base frames F1. The first and second support frames 210 and 310 may be formed by stacking a plurality of second base frames F2. The rail 100 may be formed by stacking a plurality of third base frames F3. The first to third base frames F1 to F3 are formed of a magnetic material.

Figure 12:
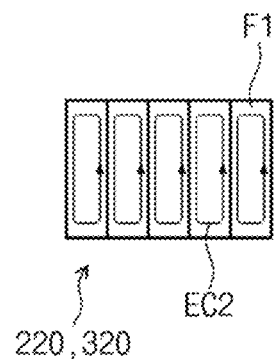
FIG. 12 is a cross sectional view of a magnetic core according to still another embodiment of the present disclosure.

The first and second magnetic cores 220 and 320 have a cylindrical shape as a whole, and the first base frames F1 have a structure in which thin plates having the same length as the first and second magnetic cores are stacked. Unlike the above, the first and second magnetic cores 220 and 320 may have a rectangular column shape. In this case, as shown in FIG. 12, the first and second magnetic cores 220 and 320 have a rectangular cross section and have a structure in which the first base frames F1 which have a plate shape and the same thickness and length are stacked.

The second base frames F2 have the same radius as the first and second support frames 210 and 220 and are provided as a ring-shaped plate having a thin thickness, and their central axis is located on the same axis. The second base frames F2 are stacked on each other to constitute the first and second support frames 210 and 220.

The third base frame F3 constitutes the rail 100 by stacking thin plates having the same length in the width direction of the rail 100.

When a high-power high-frequency magnetic field is generated, eddy currents EC1 and EC2 flow through the first and second magnetic cores 220 and 320, the first and second support frames 210 and 310, and the inside of the rail 100. Such eddy currents may be a factor that decreases the intensity of the high-frequency magnetic field.

In the embodiment of FIG. 10, because the first and second magnetic cores 220 and 320, the first and second support frames 210 and 310, and the rail 100 have relatively large cross-sectional areas, the area through which the eddy current can flow increases, so that the intensity of the eddy current EC1 increases.

To the contrary, in the embodiments of FIGS. 11 and 12, the first and second magnetic cores 220 and 320, the first and second support frames 210 and 310, and the rail 100 generate the eddy currents EC2 inside base frames F1, F2 and F3, respectively. Compared with the embodiment of FIG. 10, since each of the base frames F1, F2, and F3 has a relatively small cross-sectional area, an area through which the eddy current EC2 can flow is reduced. Accordingly, the intensity of the eddy currents EC2 flowing inside the base frames F1, F2 and F3 may be reduced, and an effect of reducing the magnetic field intensity due to the eddy current may be reduced.

Figure 13:
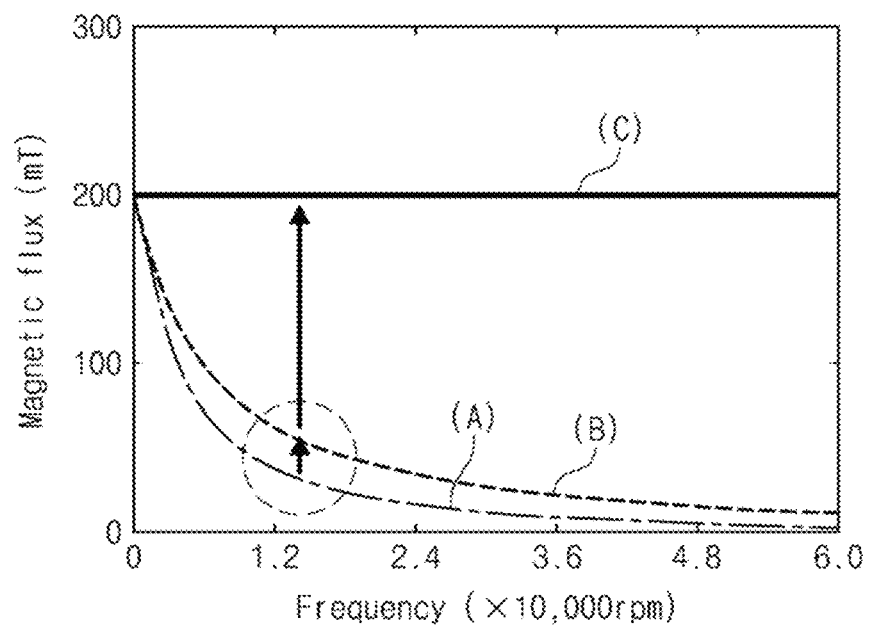
FIG. 13 is a graph showing the results of analytically calculating the intensity of a magnetic field that may be generated when a high-frequency magnetic field is generated according to the application of a variable capacitor and a stacked magnetic structure.

FIG. 13 is a graph showing the results of analytically calculating the intensity of a magnetic field that may be generated when a high-frequency magnetic field is generated according to the application of a variable capacitor and a stacked magnetic structure. A first graph A shows the intensity of the magnetic field according to an embodiment in which a variable capacitor and a stacked magnetic structure are not applied, A second graph B shows the intensity of a magnetic field according to an embodiment in which a variable capacitor is applied and a stacked magnetic structure is not applied, as shown in FIG. 10. A third graph C shows the intensity of a magnetic field according to an embodiment in which both a variable capacitor and a stacked magnetic structure are applied as shown in FIG. 11.

Referring to FIG. 13, the resistance of the magnetic field generation unit is set to about 8Ω and the inductance is set to about 0.8 H, and the current intensity is applied to generate a magnetic field of about an intensity of 200 mT in the target area. Comparing the results according to the respective embodiments, it may be understood that the difference in the intensity of the magnetic field which is able to be generated increases rapidly as the frequency of the magnetic field increases. Accordingly, it may be understood that a variable capacitor and a stacked magnetic structure are essential in order to generate a high-power high-frequency magnetic field.

Figure 14:
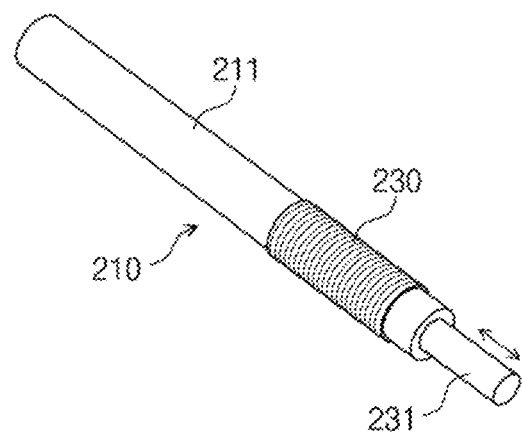
FIG. 14 is a view showing the first and second magnetic cores according to another embodiment of the present disclosure. 13
Figure 15:
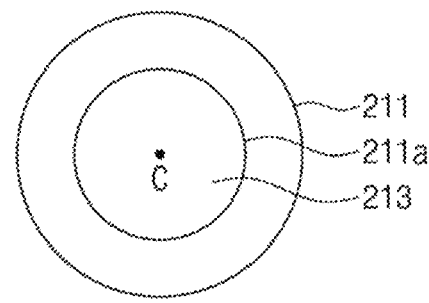
FIG. 15 is a front view showing the first and second magnetic cores of FIG. 14.

FIG. 14 is a view showing the first and second magnetic cores according to another embodiment of the present disclosure. FIG. 15 is a front view showing the first and second magnetic cores of FIG. 14. The first and second magnetic cores may be provided in the same structure. An example of the first magnetic core will be described below.

Referring to FIGS. 14 and 15, the first magnetic core 220 includes a first core housing 211, a first auxiliary core 213, and a first core driving unit (not shown).

The first core housing 211 has a first coil 230 wound on an outer surface thereof, and a space is formed therein. An opening 211a is formed at one end of the first core housing 211. The opening 211a communicates with the inside of the first core housing 211.

The first auxiliary core 213 has a volume smaller than that of the first core housing 211 and is inserted into the first core housing 211 through the opening 211a. The first auxiliary core 213 is formed of a magnetic material. According to an embodiment, the first auxiliary core 213 may have a column shape having a diameter corresponding to the opening 211a. The central axis C of the first auxiliary core 213 may be positioned on the same lien as the central axis C of the first core housing 211.

The first core driving unit linearly moves the first auxiliary core 213 in the direction of the central axis C. Accordingly, the front end of the first auxiliary core 213 may be located at the same point as one end of the first core housing 211 or may protrude forward of the first core housing 211.

The magnetic field generated by the first coil 230 flows along the first core housing 211 and the first auxiliary core 213 to generate a magnetic field in the target area T. The location of the end of the first magnetic core 210 may be changed according to the linear movement of the first auxiliary core 213, and accordingly, the intensity and distribution of the magnetic field that can be generated may be variously adjusted. In addition, by moving the first auxiliary core 213 having a relatively small weight, it is possible to minimize the occurrence of a load according to the movement.

Figure 16:
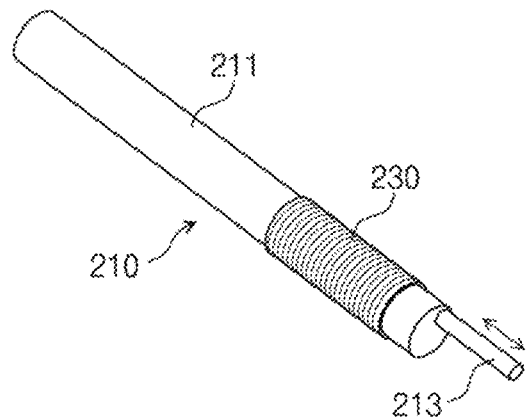
FIG. 16 is a perspective view showing a first magnetic core according to still another embodiment of the present disclosure.
Figure 17:
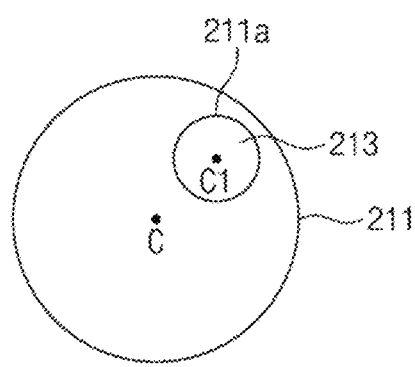
FIG. 17 is a front view showing the first magnetic core of FIG. 16.

FIG. 16 is a perspective view showing a first magnetic core according to still another embodiment of the present disclosure. FIG. 17 is a front view showing the first magnetic core of FIG. 16.

Referring to FIGS. 16 and 17, the first auxiliary core 213 has a central axis C1 spaced apart from the central axis C of the first core housing 211 by a predetermined distance, so that the central axis C1 of the first auxiliary core 213 is arranged parallel to the central axis C of the first core housing 211. The first auxiliary core 213 is linearly moved in the direction of the central axis C1 by the first core driving unit.

Figure 18:
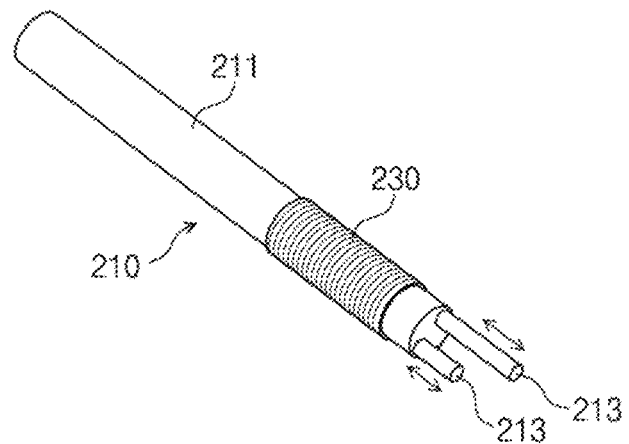
FIG. 18 is a perspective view showing a first magnetic core according to still another embodiment of the present disclosure.
Figure 19:
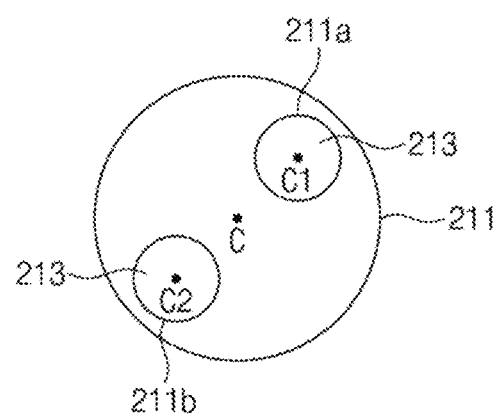
FIG. 19 is a front view showing the first magnetic core of FIG. 18.
Figure 20:
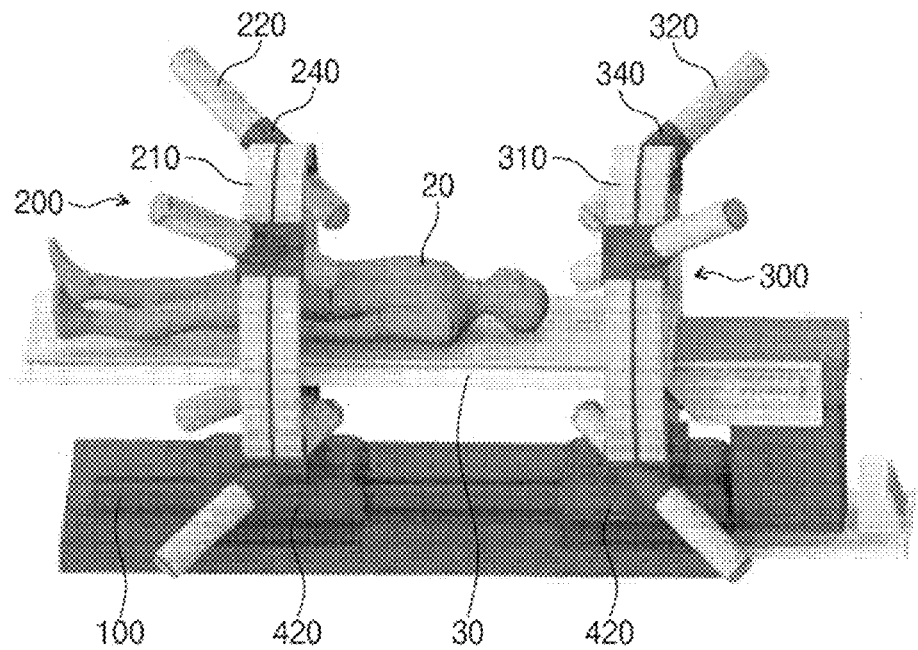
FIGS. 20 to 23 are views sequentially illustrating a method of driving a magnetic field drive system according to an embodiment of the present disclosure.
Figure 21:
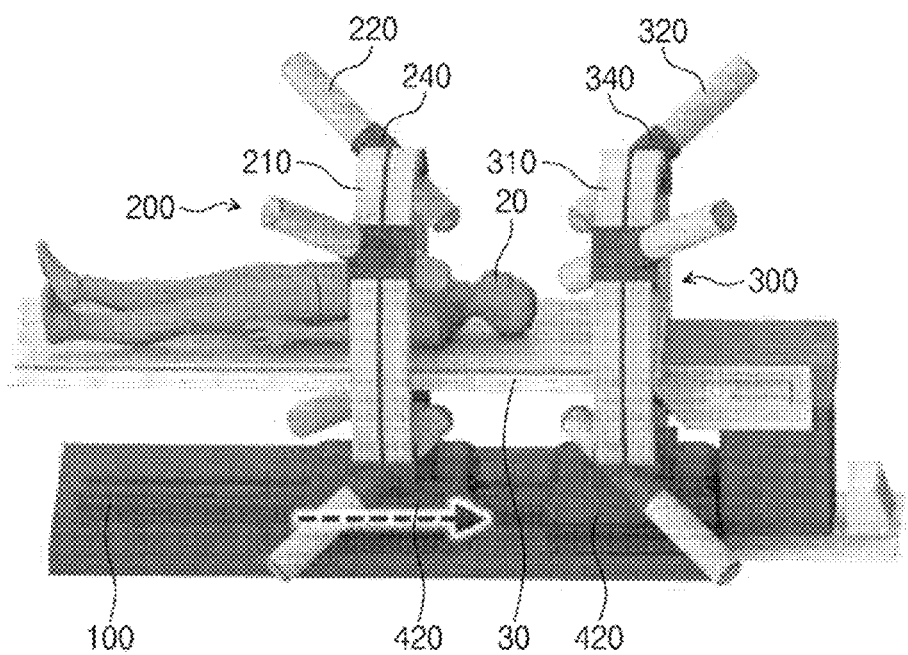
Figure 22:
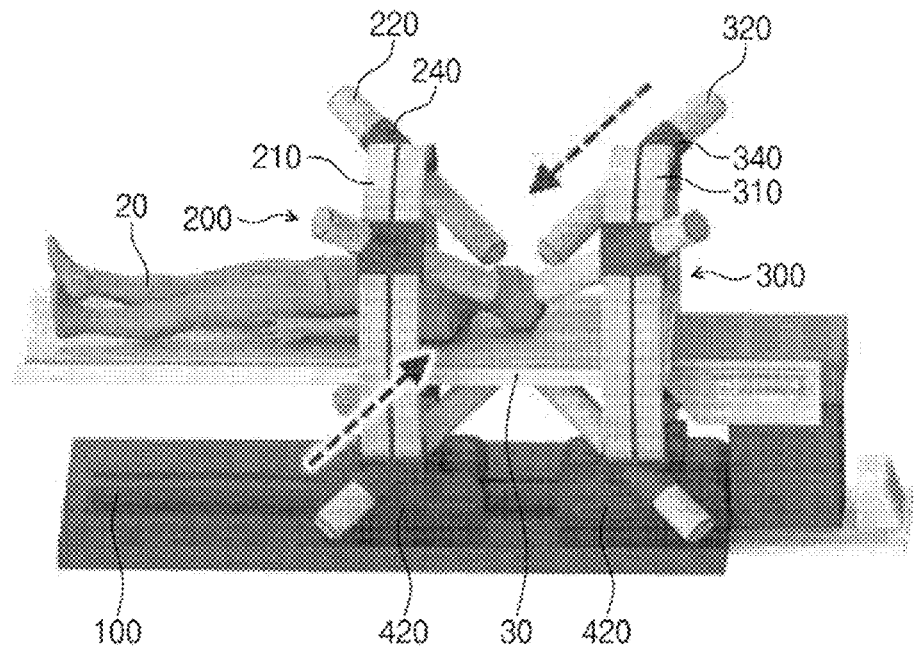
Figure 23:
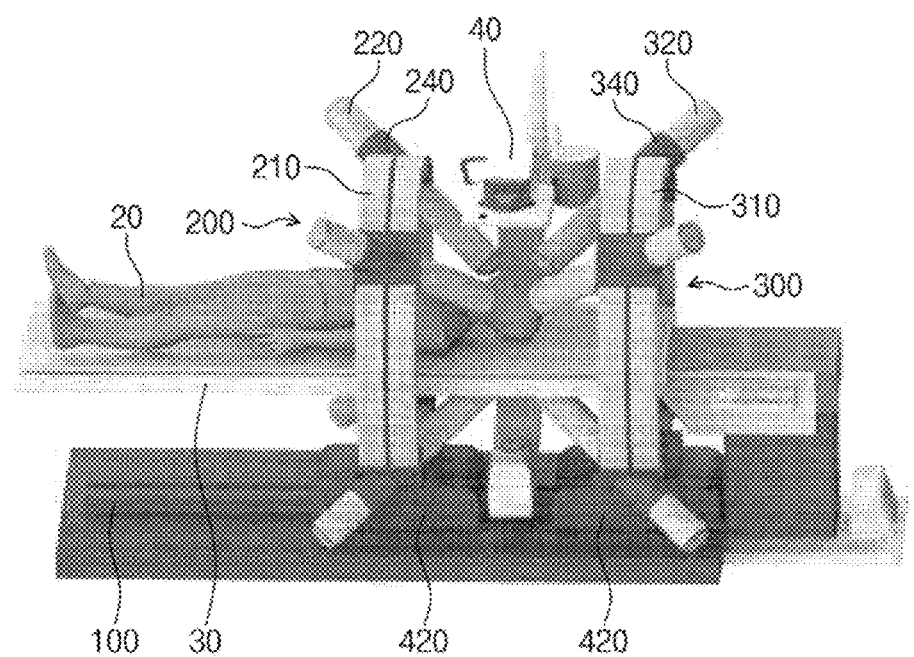

FIG. 18 is a perspective view showing a first magnetic core according to still another embodiment of the present disclosure. FIG. 19 is a front view showing the first magnetic core of FIG. 18.

Referring to FIGS. 18 and 19, a plurality of openings 211a and 211b may be formed in one end of the first core housing 211. The openings 211a and 211b may have the same size. Alternatively, the openings 211a and 211b may have different sizes. According to an embodiment, two openings 211a and 211b may be formed in one end of the first core housing 211, and each of the openings 211a and 211b may have the same size.

The first auxiliary cores 213 are inserted into the openings 211a and 211b, respectively. The first auxiliary cores 213 have diameters corresponding to the inserted openings 211a and 211b. The first central axes C1 and C2 of the auxiliary cores 213 are spaced apart from the central axis C of the first core housing 211 by a predetermined distance, so that the first central axes C1 and C2 are arranged parallel to the central axis C of the first core housing 211.

The first core drive unit linearly moves the first auxiliary cores 213 individually in the direction of their central axes C1 and C2. Accordingly, the lengths of the first auxiliary cores 213 protruding in front of the first core housing 211 may be adjusted.

FIGS. 20 to 23 are views sequentially illustrating a method of driving a magnetic field drive system according to an embodiment of the present disclosure.

Referring to FIGS. 20 to 23, a method of driving the magnetic field drive system 10 first places a patient 20 on a bed 30. In addition, the positions of the first and second magnetic field generation units 200 and 300 are adjusted such that the lesion portion of the patient 20 is located in the target area of the magnetic field drive system 10. In the present embodiment, the head region of the patient 20 is located in the target area for the treatment of brain disease of the patient 20. By driving of the first and second driving units 410 and 420, the first and second magnetic field generation units 200 and 300 move linearly along the rail 100 to cause a lesion portion of the patient 20 to located in the target area. The first and second core variable modules 240 and 340 move the first and second magnetic cores 220 and 320 along the first and second support frames 210 and 310, and move the first and second magnetic cores linearly in the direction of the central axis to align the positions of the first and second magnetic cores 220 and 320. Thus, the target area may be optimized to be suitable to the lesion portion. While an x-ray imaging apparatus 40 is positioned, power is applied to the first and second coils 230 and 330. When power is applied, a magnetic field is generated in the target area. The position of a magnetic robot inserted into the body of the patient 20 is tracked based on the perspective image obtained by the x-ray imaging apparatus 40, and the movement of the magnetic robot moves may be controlled by using the magnetic field generated by the magnetic field drive system 10. As described above, the intensity of the magnetic field generated in the target area may be increased by the formation of the closed magnetic circuit.

Figure 24:
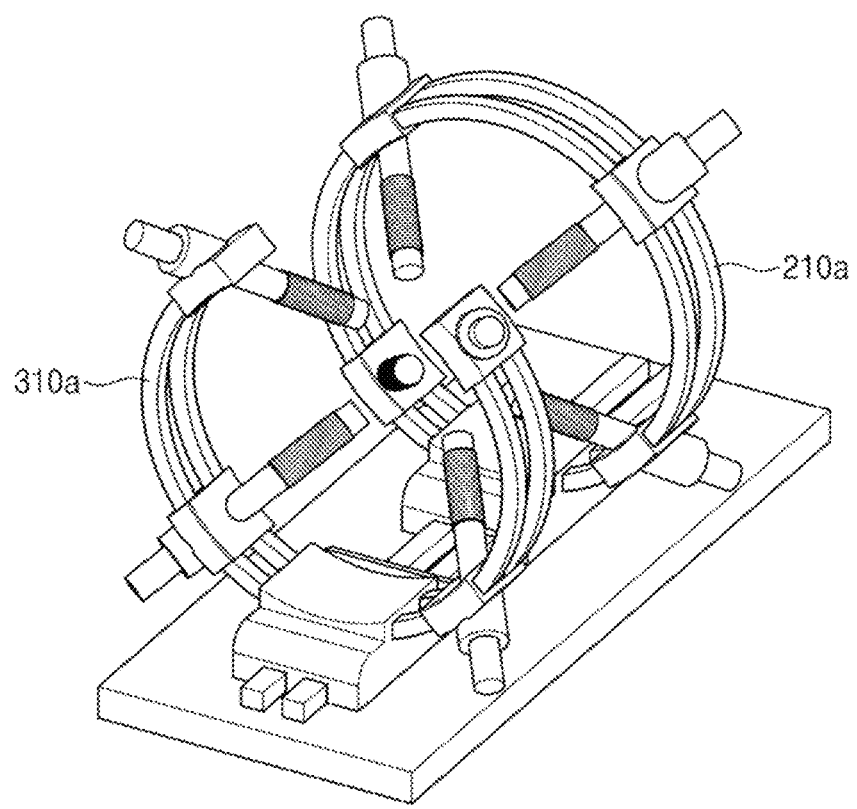
FIGS. 24 to 26 are perspective views showing magnetic field driving systems according to various embodiments of the present disclosure.
Figure 25:
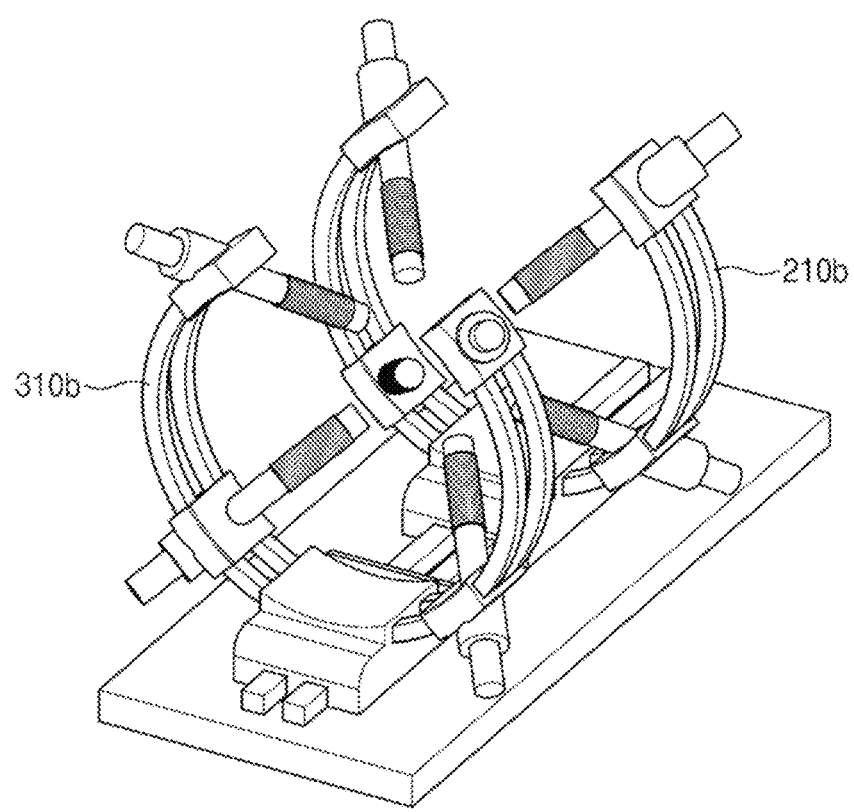
Figure 26:
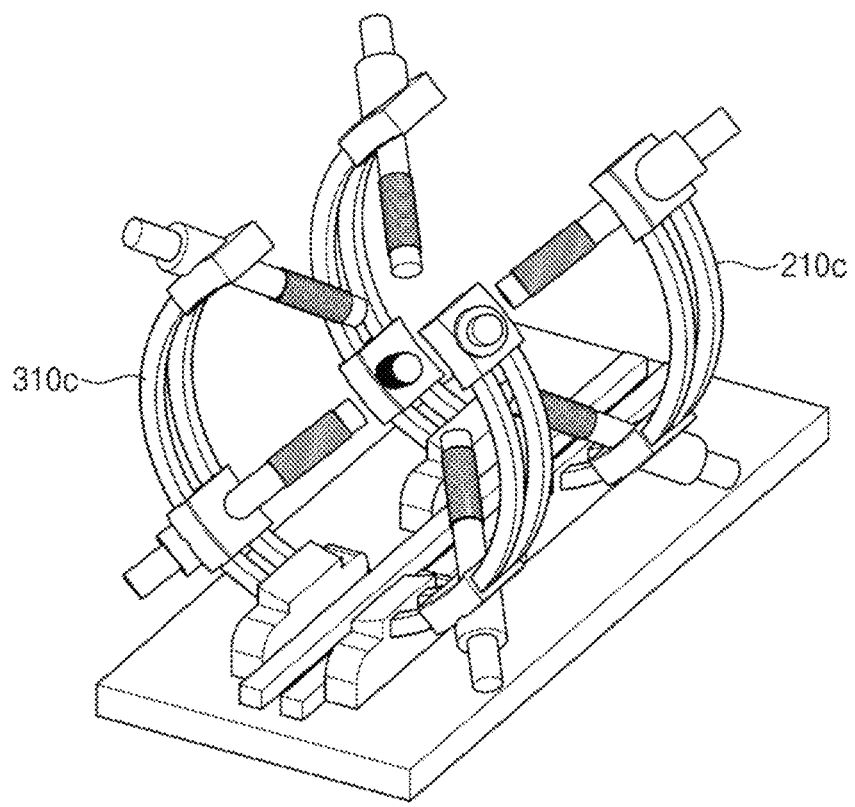

FIGS. 24 to 26 are perspective views showing magnetic field driving systems according to various embodiments of the present disclosure.

Referring to FIGS. 24 to 26, the first and second support frames of the magnetic field drive system may have a ring or arc shape. Referring to FIG. 24, the first support frame 210a may have a ring shape, and the second support frame 310a may have an arc shape having an open top. Referring to FIG. 25, both of the first and second support frames 210b and 310b may have an arc shape having an open top. Referring to FIG. 26, both of the first and second support frames 210c and 310c may have an arc shape in which upper and lower portions are open. The combination of the first and second support frames is not limited thereto, and may be changed to various combinations of the above-described ring and arc shapes.

The shapes of the first and second support frames 210a to 210c and 310a to 310c described above maximize compatibility between an x-ray imaging apparatus including a C-arm and a magnetic field drive system. In addition, the first and second support frames 210a to 210c and 310a to 310c are lightened in weight.

As described above, although the present disclosure has been described in detail using preferred embodiments, the scope of the present disclosure is not limited to specific embodiments, and should be interpreted by the appended claims. In addition, it should be understood that various modifications and alterations can be made from the disclosures above by a person having ordinary skill in the art, without departing from the scope of the present disclosure.

INDUSTRIAL APPLICABILITY

The magnetic field drive system according to the present disclosure may drive a magnetic robot by generating a magnetic field in a target area.

The invention claimed is:

1. A magnetic field drive system comprising:
a rail;
a first magnetic field generation unit installed on the rail; and
a second magnetic field generation unit installed on the rail while facing the first magnetic field generation unit with a target area interposed therebetween,
wherein the first and second magnetic field generation units generate a magnetic field in the target area,
wherein the first magnetic field generation unit includes:
a first support frame installed on the rail;
at least one first magnetic core supported by the first support frame and having ends disposed toward the target area; and
a first coil wound around each of the first magnetic cores,
wherein the second magnetic field generation unit includes:
a second support frame installed on the rail while facing the first support frame;
at least one second magnetic core supported by the second support frame and having ends disposed toward the target area; and a second coil wound around each of the second magnetic cores,
wherein the first and second magnetic cores, the first and second support frames and the rail are formed of a magnetic material, and
wherein the magnetic field formed in the target area, and magnetic fields formed in the first magnetic core, the first support frame, the rail, the second support frame and the second magnetic core, respectively, constitute a closed magnetic circuit.

2. The magnetic field drive system of claim 1, further comprising:
a driving unit configured to move the first and second magnetic field generation units along the rail.

3. The magnetic field drive system of claim 1, wherein the first magnetic field generation unit includes a first core variable module configured to move the first magnetic core along the first support frame, and
wherein the second magnetic field generation unit includes a second core variable module configured to move the second magnetic core along the second support frame.

4. The magnetic field drive system of claim 3, wherein the first core variable module is configured to individually move the first magnetic cores, and
the second core variable module is configured to individually move the second magnetic cores.

5. The magnetic field drive system of claim 3, wherein the first core variable module is configured to linearly move the first magnetic core in a direction of a central axis of the first magnetic core, and
the second core variable module is configured to linearly move the second magnetic core in a direction of a central axis of the second magnetic core.

6. The magnetic field drive system of claim 3, wherein the first and second support frames have ring or arc shapes, respectively, and centers thereof are located on a same axis.

7. A magnetic field drive system comprising:
a rail;
a first magnetic field generation unit installed on the rail; and
a second magnetic field generation unit installed on the rail while facing the first magnetic field generation unit with a target area interposed therebetween,
wherein the first and second magnetic field generation units generate a magnetic field in the target area,
wherein the first magnetic field generation unit includes:
a first support frame installed on the rail;
at least one first magnetic core supported by the first support frame and having ends disposed toward the target area; and
a first coil wound around each of the first magnetic cores,
wherein the second magnetic field generation unit includes:
a second support frame installed on the rail while facing the first support frame;
at least one second magnetic core supported by the second support frame and having ends disposed toward the target area; and
a second coil wound around each of the second magnetic cores, and
wherein the magnetic field drive system further includes:
a power supply unit configured to supply power to the first coil through a first circuit and supply power to the second coil through a second circuit; and
variable capacitors provided in the first circuit and the second circuit, respectively.

8. A magnetic field drive system comprising:
a rail;
a first magnetic field generation unit installed on the rail; and
a second magnetic field generation unit installed on the rail while facing the first magnetic field generation unit with a target area interposed therebetween,
wherein the first and second magnetic field generation units generate a magnetic field in the target area,
wherein the first magnetic field generation unit includes:
a first support frame installed on the rail;
at least one first magnetic core supported by the first support frame and having ends disposed toward the target area; and
a first coil wound around each of the first magnetic cores,
wherein the second magnetic field generation unit includes:
a second support frame installed on the rail while facing the first support frame;
at least one second magnetic core supported by the second support frame and having ends disposed toward the target area; and
a second coil wound around each of the second magnetic cores, and
wherein the first support frame has a structure in which a plurality of base frames formed of a magnetic material are stacked.

9. The magnetic field drive system of claim 8, wherein the base frames have a same radius as the first support frame, and are located on a same central axis.

10. A magnetic field drive system comprising:
a rail;
a first magnetic field generation unit installed on the rail; and
a second magnetic field generation unit installed on the rail while facing the first magnetic field generation unit with a target area interposed therebetween,
wherein the first and second magnetic field generation units generate a magnetic field in the target area,
wherein the first magnetic field generation unit includes:
a first support frame installed on the rail;
at least one first magnetic core supported by the first support frame and having ends disposed toward the target area; and
a first coil wound around each of the first magnetic cores,
wherein the second magnetic field generation unit includes:
a second support frame installed on the rail while facing the first support frame;
at least one second magnetic core supported by the second support frame and having ends disposed toward the target area; and
a second coil wound around each of the second magnetic cores,
wherein the first magnetic core has a structure in which a plurality of base frames formed of a magnetic material are stacked, and
wherein the base frames have a same length as the first magnetic core.

11. A magnetic field drive system comprising:
a rail;
a first magnetic field generation unit installed on the rail; and
a second magnetic field generation unit installed on the rail while facing the first magnetic field generation unit with a target area interposed therebetween,
wherein the first and second magnetic field generation units generate a magnetic field in the target area,
wherein the first magnetic field generation unit includes:
a first support frame installed on the rail;
at least one first magnetic core supported by the first support frame and having ends disposed toward the target area; and
a first coil wound around each of the first magnetic cores,
wherein the second magnetic field generation unit includes:
a second support frame installed on the rail while facing the first support frame;
at least one second magnetic core supported by the second support frame and having ends disposed toward the target area; and
a second coil wound around each of the second magnetic cores,
wherein the rail has a structure in which a plurality of base frames formed of a magnetic material are stacked, and
wherein the base frames have a same length as the rail.

12. The magnetic field drive system of claim 1, wherein the first magnetic core includes:
a first core housing having an outer side surface around which the first coil is wound, an inner space, and one end in which an opening is formed;
a first auxiliary core inserted into the inner space through the opening; and
a first core driving unit configured to linearly move the first auxiliary core in a central direction thereof.

13. The magnetic field drive system of claim 12, wherein a central axis of the first core housing and a central axis of the first auxiliary core are located on a same line.

14. The magnetic field drive system of claim 12, wherein a central axis of the first core housing is parallel with a central axis of the first auxiliary core.

15. The magnetic field drive system of claim 12, wherein a plurality of openings are formed at one end of the first core housing,
a plurality of first auxiliary cores are inserted into the openings, respectively, and
the first core driving unit is configured to individually move the first auxiliary cores.

16. The magnetic field drive system of claim 15, wherein the openings have mutually different sizes, and
the first auxiliary cores have sizes corresponding to the openings, respectively.

* * * * *